United States Patent [19]

Fauran et al.

[11] 4,211,772

[45] Jul. 8, 1980

[54] BENZOPYRAN GLYCOSIDE ACETALS AND KETALS

[75] Inventors: François Fauran, Castanet-Tolosan; Claude Feniou, Pessac; Jacqueline Mosser, St-Medard-en-Jalles; Annie Thibault, Le Bouscat; Claude Andre, Fontaine; Gisele Prat, Talence, all of France

[73] Assignee: Laboratoires Sarget, Merignac, France

[21] Appl. No.: 911,634

[22] Filed: Jun. 1, 1978

[30] Foreign Application Priority Data

Jun. 2, 1977 [FR] France .................................. 77 16817
May 10, 1978 [FR] France .................................. 78 13807
May 10, 1978 [FR] France .................................. 78 13808

[51] Int. Cl.$^2$ ........................ A61K 31/70; C07H 17/06
[52] U.S. Cl. ...................................... 424/180; 536/8; 536/4
[58] Field of Search ..................... 536/8, 1, 23, 24, 26; 424/180

[56] References Cited

U.S. PATENT DOCUMENTS

| | | | |
|---|---|---|---|
| 3,420,815 | 1/1969 | Courbat et al. ............................ | 536/8 |
| 3,422,086 | 1/1969 | Carron et al. ............................. | 536/8 |
| 3,607,862 | 9/1971 | Jaffe et al. ................................. | 536/1 |
| 3,888,842 | 6/1975 | Capaux et al. ............................ | 536/8 |

OTHER PUBLICATIONS

Griffin, B., et al., Tetrahedron, 1967, 23, 2301.
Reese, C., et al., J. Chem. Soc., Perkin Trans. I(GB), No. 10, 1975 (934–942).

*Primary Examiner*—Johnnie R. Brown
*Assistant Examiner*—Blondel Hazel
*Attorney, Agent, or Firm*—Oblon, Fisher, Spivak, McClelland & Maier

[57] ABSTRACT

Acetals and ketals of benzopyran glycosides, prepared by condensing a benzopyran glycoside with a carbonyl compound using a chloroformate ester as condensing agent, show enhanced activity in treating capillary fragility and related pathologies, as well as effectiveness in modifying the evolution of diabetic cataracts.

9 Claims, 2 Drawing Figures

FIG. 1  250MHz NMR SPECTRUM ACETYLATED RUTIN

BENZOPYRAN GLYCOSIDE ACETALS AND KETALS

BACKGROUND OF THE INVENTION

1. Field of the Invention

The present invention relates to new derivatives of benzopyrene glycosides, their method of production as well as their use in human therapy.

2. Description of the Prior Art

The benzopyran glycosides form a class of compounds containing derivatives such as rutin, hesperidin, esculin, and naringin, and which exhibit multiple pharmacological and biological properties, among which is a reduction of capillary fragility, which is often related to their inhibitory activity with respect to catechol O-methyl transferase, and which is generally associated with an anti-edemic activity. Certain of these derivatives are also inhibitors of aldose reductase, an enzyme which has been implicated in particular in the development of cataracts and neuropathies among diabetics. Certain of these compounds are employed in therapy, most often in the treatment of capillary fragility.

Several partial synthetic procedures have been developed by various laboratories for the purpose of preparing derivatives which are more active or which present improved physicochemical properties, such as greater solubility in water. Examples of procedures for etherification of one or more phenolic functions of the quercetin nucleus of rutin include etherification by hydroxyethyl groups (hydroxyethyl rutoside), methyl groups (methyl rutin), and morpholinoethyl groups (ethoxazorutin).

These methods have the disadvantage of leading to more or less well defined mixtures and of blocking one or more phenolic OH functions. Thus, the hydroxyethylation of rutin leads to a mixture containing as major constituents the 5, 7, 4'-tri-O-hydroxyethyl, 7, 3', 4'-tri-O-hydroxyethyl, 5, 7, 3',4'-tetra-O-hydroxyethyl, 7, 4'-di-O-hydroxyethyl and 4'-mono-O-hydroxyethyl derivatives. Furthermore, since rutin inhibits aldose reductase in vitro, the derivatives in which one or more phenolic OH groups are blocked, such as 7-O-hydroxyethyl rutin, 7, 3', 4'-tri-O-hydroxyethyl rutin and 5, 7, 3', 4'-tetra-O-hydroxyethyl rutin are practically inactive.

A need therefore continues to exist for derivatives of benzopyran glycosides having improved pharmacological and biological activity and improved properties such as greater solubility in water, without diminishing aldose reductase inhibitory activity. A need also exists for a method for preparing specific derivatives of benzopyran glycosides as pure compounds.

SUMMARY OF THE INVENTION

Accordingly, one object of the invention is to provide derivatives of benzopyran glycosides having antiedemic activity, capillary fragility reducing activity and aldose reductase inhibitory activity.

Another object of the invention is to provide derivatives of benzopyran glycosides having greater water solubility.

A further object of the invention is to provide a method for producing specific derivatives of benzopyran glycosides having well defined structures and characterized in that only the sugar portion of the molecule is derivatized, leaving phenolic hydroxyl groups unaffected.

Briefly, these objects and other objects of the invention as hereinafter will become more readily apparent can be attained by providing a benzopyran gylcoside acetal or ketal which is a condensation product of a benzopyran glycoside and a carbonyl compound selected from the group consisting of wherein $R_1$ and $R_2$ are the same or different and $R_1$, $R_2 = H$, alkyl, phenyl, phenyl substituted by one or more substituents selected from the group consisting of hydroxyl, alkoxyl, halogen, nitro, aminoalkyl, and carboxyl, but excluding $R_1 = R_2 = H$;

wherein $n = 4$–$7$; 2-adamantanone, 1-decalone, 2-decalone, and simple acetals or ketals thereof; and a method of preparing the same.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

A new partial synthetic procedure has now been developed permitting the preparation, starting with a given benzopyran glycoside, of a compound which is well defined and which retains its free phenolic groups. The new products thus obtained show pharmacological and biological activities of great interest. They not only possess the classic activities of benzopyran glycosides, such as reduction of capillary fragility and anti-edemic action, but they also show inhibitory affects on aldose reductase which occur in vitro at concentrations much lower than that of their homologues. This biological property is retained in vivo, and in particular manifests itself by a modification of the evolution of galactosemic cataracts in rats.

The new partial synthetic procedure consists of reacting a carbonyl derivative with a benzopyran glycoside under particular experimental conditions in order to obtain an acetal or ketal which only involves the sugar portion of the molecule. The carbonyl derivative may be chosen from the group wherein $R_1$ and $R_2$ are the same or different and $R_1$, $R_2$ equals H, alkyl, phenyl, phenyl substituted by one or more substituents preferably chosen from the group consisting of hydroxy, alkoxy, halogen, nitro, amino, alkyl, and COOH; with $R_1=R_2=H$ excluded;

with n from 4 to 7; and condensed ring ketones preferably chosen from the group consisting of 2-adamantanone, 1-decalone and 2-decalone.

In the case where the carbonyl derivative is acetaldehyde, paraldehyde is preferably used. The carbonyl compound may also be replaced by one of its derivatives, such as a dimethyl or diethyl acetal or ketal.

The benzopyran glycosides are preferably chosen from the group consisting of myricitrin, esculin, hesperidin, naringin, diosmin and glycosides of quercetin.

The preparation of these new derivatives can be achieved using classical techniques for the synthesis of sugar acetals or ketals; the synthesis generally involves the condensation of a carbonyl compound under anhydrous conditions in the presence of a catalyst which can consist for example of a mineral acid such as concentrated sulfuric acid, a cation exchange resin, anhydrous zinc chloride, or anhydrous copper (II) sulfate. However, a new synthetic procedure has now been discovered for the synthesis of these acetals or ketals characterized by the use as a condensing agent of ethyl, methyl or benzyl chloroformate.

This method makes it possible to work at lower temperatures than the classical methods, which avoids the risk of breaking the aglycone-sugar linkage of the benzopyran glycoside.

The following general method is used to prepare the compounds of the present invention: the benzopyran glycoside is first dissolved in a polar solvent, preferably dimethylformamide; into this solution is introduced the carbonyl derivative, after which is introduced with stirring methyl, ethyl or benzyl chloroformate. The acetal or ketal thus formed is afterwards recovered and eventually purified by conventional methods.

Certain acetals or ketals thus obtained are more soluble in water than the benzopyran glycosides from which they are derived. They may therefore be advantageously used in place of the latter in the case where a particular solubility in water is necessary, for example, when it is desired to administer these compounds in an injectable form.

Having generally described this invention, a further understanding can be obtained by reference to certain specific examples which are provided herein for purposes of illustration only and are not intended to be limiting unless otherwise specified.

EXAMPLE 1

Rutin Acetonide (Compound No. 1)

15 grams of rutin are dissolved in 60 cc of dimethylformamide. After addition of 100 cc of acetone, 15 cc of methyl chloroformate are added dropwise while agitating the mixture. Since the reaction is exothermic, the mixture is maintained at ambient temperature with cooling. At the end of 6 hours, the mixture is evaporated under vacuum. The residue is taken up in 500 cc of water. The solution is extracted with ether. The residual aqueous phase is extracted with ethyl acetate. After evaporation of the organic phase, about 10 grams of rutin acetonide is obtained, which can then be recrystallized.

Figure 1:
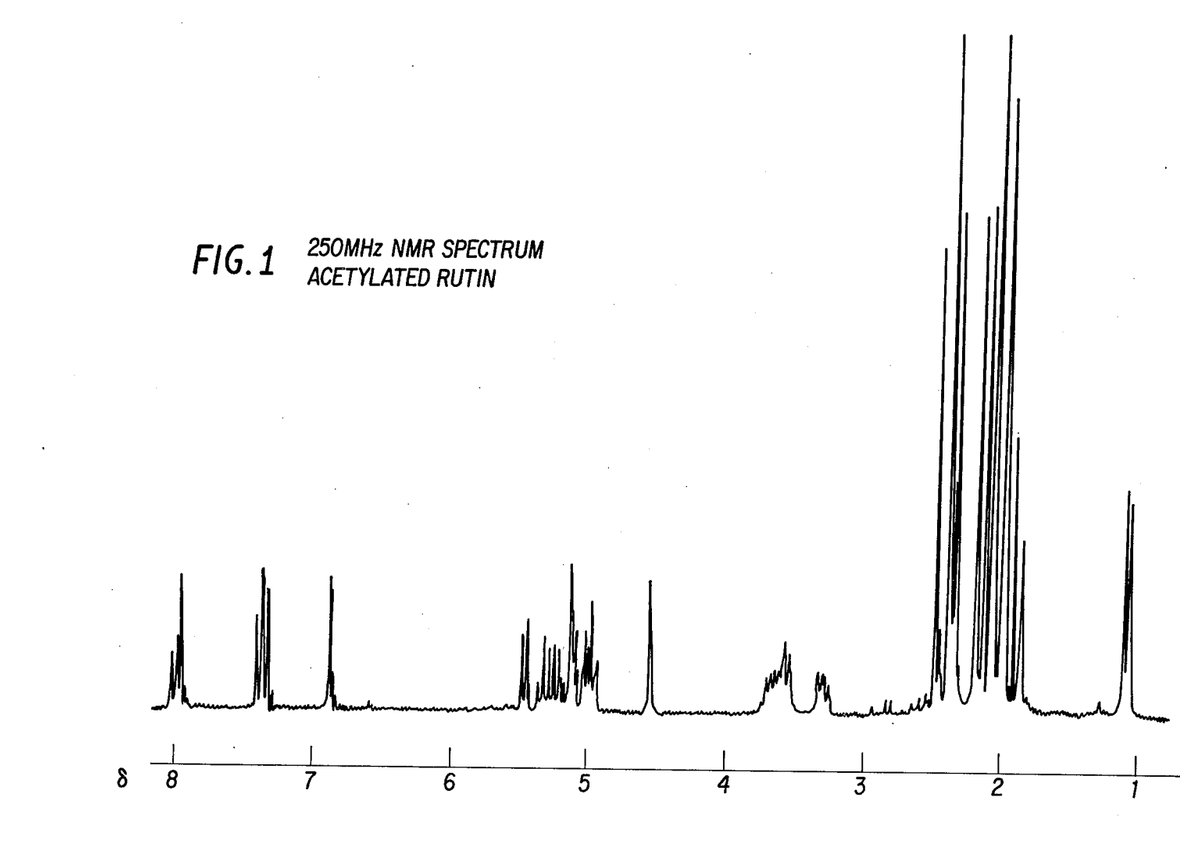
FIG. 1 is a 250 MHz NMR spectrum of acetylated rutin in $CDCl_3$.
Figure 2:
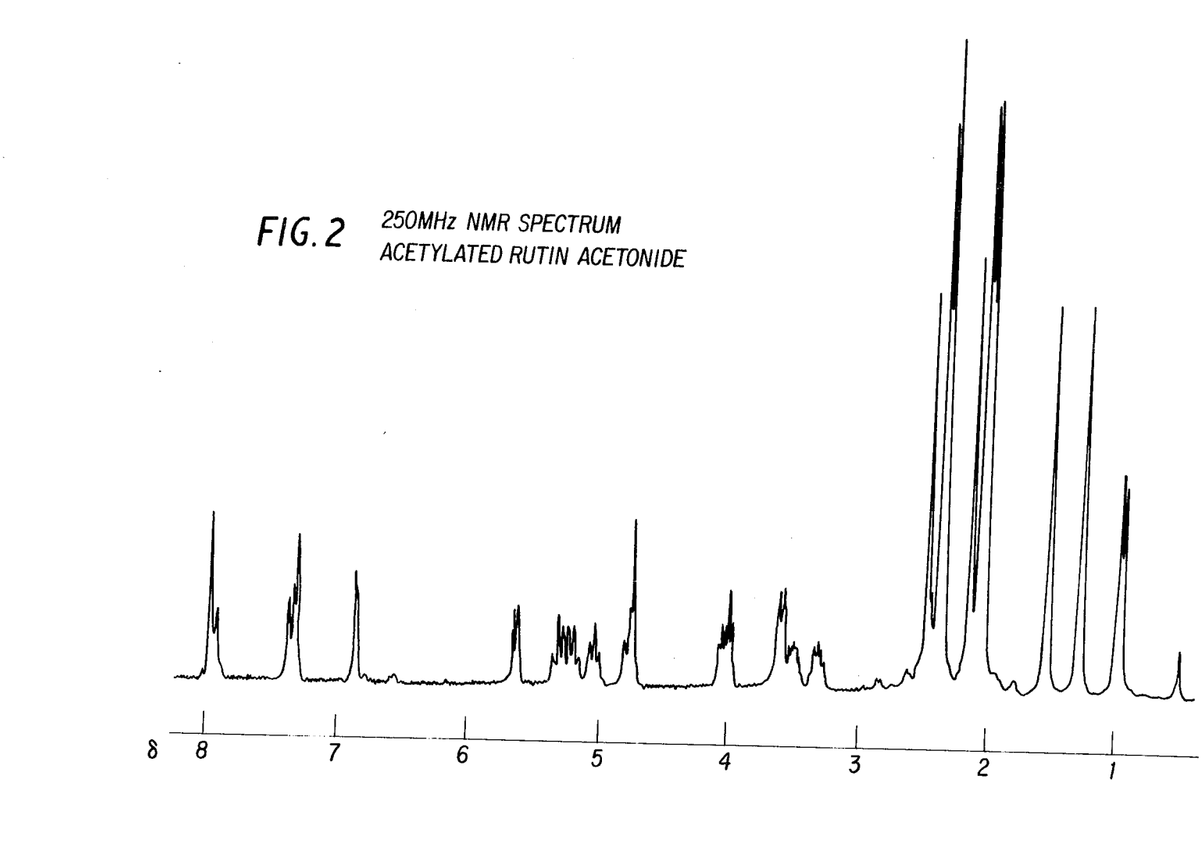
FIG. 2 is a 250 MHz NMR spectrum of acetylated rutin acetonide in $CDCl_3$.

The structure of this compound was determined by high resolution NMR and by mass spectroscopy as follows:

The 250 MHz NMR spectrum of acetylated rutin and of acetylated rutin acetonide, in CDCl$_3$, were compared. These two spectra are shown in FIGS. 1 and 2. This comparison provides evidence that the spectrum of acetylated compound No. 1 shows the presence of two C—CH$_3$ groups at 1.29 and 1.54 ppm, of 12 protons between 3.2 and 5.7 ppm with chemical shifts and coupling constants different from those of acetylated rutin, as well as the absence of two acetylated alcoholic groups at around 2 ppm. Decoupling experiments permitted the assignment of various signals to the protons of the sugars and demonstrated that the acetonide is formed using the 2-OH and 3-OH of the rhamnose.

The mass spectrum shows, besides peaks corresponding to the fragmentation of 5, 7, 3', 4'-tetra-acetylated quercetin, a peak at m/e 229 corresponding to acetylated rhamnose acetonide and representing the base peak of the spectrum, and a peak at m/e 171 corresponding to rhamnose acetonide. The molecular ion peak is nearly invisible.

These physicochemical data are in accord with the following structure:

EXAMPLE 2

Esculin Acetonide (Compound No. 15)

A solution of 10 grams of esculin, 50 cc of dimethylformamide and 50 cc of acetone is cooled to 0° C. While maintaining the temperature at 0° C., 10 cc of methyl chloroformate are added dropwise. This procedure is repeated at the end of 3 hours. The mixture is kept overnight at ambient temperature with agitation. It is then cooled to 0° C. and neutralized with a minimum quantity of methanolic sodium hydroxide. The solvents are removed by evaporation and the residue is dissolved in water. The acetonide is extracted with ethyl acetate. The ethyl acetate extracts are dried and evaporated. The crude product is purified by column chromotography on polyamide SC6. The acetonide is then dried under vacuum at 100° C.

EXAMPLE 3

Rutin Adamantanone Ketal (Compound No. 33)

A solution of 10 grams of rutin, 10 grams of 2-adamantanone and 50 cc of dimethylformamide is cooled to 0° C. While maintaining the temperature at 0° C., 10 cc of methyl chloroformate are added dropwise. This procedure is repeated at the end of 3 hours. The mixture is kept at ambient temperature for 14 hours with agitation, and is then poured into 150 cc of aqueous methanolic sodium hydroxide kept at 0° C. The solvents are removed by evaporation to dryness and the residue is washed with benzene to recover excess adamantanone, then the residue is dissolved in water and neutralized with 10% acetic acid to pH 6. The ketal precipitates. After drying and filtration, it is purified by passage through a polyamide column. The yield is 80%, based on rutin.

The compounds of the present invention are all prepared by the above methods. The structures and physicochemical characteristics of representative acetals and ketals thus obtained are shown below.

FORMULA

No. 1 3-O-(2,3-O,O-isopropylidene-6-α-L-rhamnosyl-β-D-glucosyl)-quercetin

No. 3 3-O-(2,3-O,O-isopropylidene-α-L-rhamnosyl)-quercetin

No. 4 3-O-(3,4-O,O-isopropylidene-6-α-L-arabinosyl-β-D-glucosyl)-quercetin

No. 5 3-O-(4,6-O,O-isopropylidene-β-D-glucosyl)-quercetin

No. 6 3-O-(2,3-O,O-cyclohexylidene-6-α-L-rhamnosyl-β-D-glucosyl)-quercitin

No. 7 3-O-(2,3-O,O-cyclohexylidene-α-L-rhamnosyl)-quercetin

No. 8 7-O-(2,3-O,O-isopropylidene-2-α-L-rhamnosyl-β-D-glucosyl)-naringenin

No. 14 3-O-(2,3-O,O-isopropylidene-α-L-rhamnosyl)-myricitin

No. 15 6-O-(4,6-O,O-isopropylidene-β-D-glucosyl) esculetol

No. 16 6-O-(4,6-O,O-cyclohexylidene-β-D-glucosyl) esculetol

No. 18 7-O-(2,3-O,O-isopropylidene-6-α-L-rhamnosyl-β-D-glucosyl) hesperitin

No. 22 3-O-(2,3-O,O-p-methoxybenzylidene-6-α-L-rhamnosyl-β-D-glucosyl) quercetin No. 23 3-O-(2,3-O,O-p-hydroxybenzylidene-6-α-L-rhamnosyl-β-D-glucosyl)quercetin No. 24 6-O-(4,6-O,O-(3,4-dihydroxybenzylidene)-β-D-glucosyl) esculetol No. 28 3-O-(2,3-O,O-(2-perhydronaphthylidene)-6-α-L-rhamnosyl-β-D-glucosyl) quercetin No. 32 7-O-(2,3-O,O-isopropylidene-6-α-L-rhamnosyl-β-D-glucosyl) diosmitin No. 33 3-O-(2,3-O,O-adamantylidene-6-α-L-rhamnosyl-β-D-glucosyl) quercetin No. 35 3-O-(2,3-O,O-(α-methyl-p-methylbenzylidene)-6-α-L-rhamnosyl-β-D-glucosyl) quercetin No. 36 3-O-(2,3-O,O-(α-methyl-p-methoxybenzylidene)-6-α-L-rhamnosyl-β-D-glucosyl) quercetin No. 37 3-O-(2,3-O,O-(α-methyl-p-chlorobenzylidene)-6-α-L-rhamnosyl-β-D-glucosyl) quercetin No. 42 3-O-(2,3-O,O-adamantylidene-α-L-rhamnosyl) quercetin

| Proton NMR in DMSO-d-TMS internal reference. Varion EM 360 | | |
|---|---|---|
| No. 1 | 1.1 ppm | 3 H; doublet; CH$_3$ rhamnose |
| | 1.2 and 1.4 ppm | 2 × 3 H; singlets; exo- and endo- isopropylidene CH$_3$'s |
| | 2.7–5.8 ppm | 16 H; complex multiplet; CH, OH and CH$_2$ protons of the sugars |
| | 6.2 ppm | 1H; doublet; 6-H |
| | 6.4 ppm | 1 H; doublet; 8-H |
| | 6.9 ppm | 1H; doublet; 5'-H |
| | 7.4–7.7 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 3 | 0.8 ppm | 3H; doublet; CH$_3$ rhamnose |
| | 1.4 and 1.5 ppm | 2 × 3; singlets; exo- and endo- isopropylidene CH$_3$'s |
| | 2.7–5.8 ppm | 6 H; complex multiplet; CH, OH protons of the sugar, with CH$_1$ at 5.8 ppm |
| | 6.2 ppm | 1 H; doublet; 6-H |
| | 6.4 ppm | 1 H; doublet; 8-H |
| | 6.9 ppm | 1 H; doublet; 5'-H |
| | 7.3–7.6 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 4 | 1.2 and 1.3 ppm | 2 × 3 H; singlets; exo- and endo- isopropylidene CH$_3$'s |
| | 2.6–5.8 ppm | 17 H; complex multiplet; protons of the sugar |
| | 6.2 ppm | 1 H; doublet; 6-H |
| | 6.4 ppm | 1 H; doublet; 8-H |
| | 6.9 ppm | 1 H; doublet; 5'-H |
| | 7.4–7.8 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 5 | 1.3 and 1.4 ppm | 2 × 3 H; singlets; exo-and endo- isopropylidene CH$_3$'s |
| | 2.7–5.8 ppm | 9 H; complex multiplet; protons of the sugar |
| | 6.2 ppm | 1 H; doublet; 6-H |
| | 6.4 ppm | 1 H; doublet; 8-H |
| | 6.9 ppm | 1 H; doublet; 5'-H |
| | 7.4–7.8 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 6 | 1.0 ppm | 3 H; doublet; CH$_3$ rhamnose |
| | 1.0–1.9 ppm | 10 H; complex multiplet; CH$_2$ cyclohexylidene |
| | 2.7–5.8 ppm | 16 H; complex multiplet; CH, OH and CH$_2$ protons of the sugars |
| | 6.2 ppm | 1 H; doublet; 6-H |
| | 6.4 ppm | 1 H; doublet; 8-H |
| | 6.9 ppm | 1 H; doublet; 5'-H |
| | 7.4–7.7 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 7 | 0.8 ppm | 3 H; doublet; CH$_3$ rhamnose |
| | 1.0–1.9 ppm | 10 H; complex multiplet; CH$_2$ cyclohexylidene |
| | 2.7–5.7 ppm | 6 H; complex multiplet; CH, OH protons of the sugar, with CH$_1$ at 5.7 ppm |
| | 6.2 ppm | 1 H; doublet; 6-H |
| | 6.4 ppm | 1 H; doublet; 8-H |
| | 6.9 ppm | 1 H; doublet; 5'-H |
| | 7.1–7.5 ppm | 2 H; complex multiplet; 2', 6'-H |
| | 9–11 ppm | 3 H; broad peak; 3', 4', 7-OH |
| | 12.6 ppm | 1 H; singlet; 5-OH |
| NO. 8 | 1–1.7 ppm | 9 H; complex multiplet; CH$_3$ rhamnose + 2 isopropylidene CH$_3$'s |
| | 2.5–5.8 ppm | 19 H; complex multiplet; CH, OH and CH$_2$ protons of the sugars + 2,3,3-H |
| | 6–6.3 ppm | 2 H; complex multiplet; 6, 8-H |
| | 7.1 ppm | 4 H; center of an AA'BB' system; 3', 5' - 2', 6' protons |
| | 9.6 ppm | 1H; singlet; 4'-OH |
| | 12 ppm | 1 H; singlet; 5-OH |
| No. 15 | 1.3 and 1.4 ppm | 2 × 3 H; singlets; exo and endo-isopropylidene CH$_3$'s |
| | 3.2–5.4 ppm | 9 H; complex multiplet; protons of the sugar |
| | 6.2 ppm | 1 H; doublet; 3-H |
| | 6.8 ppm | 1 H; singlet; 8-H |
| | 7.4 ppm | 1 H; singlet; 5-H |
| | 7.9 ppm | 1 H; doublet; 4-H phenolic OH peak very broad |
| No. 16 | 1.1–2.2 ppm | 10 H; complex multiplet; cyclohexylidene protons |
| | 3.2–5.5 ppm | 9 H; complex multiplet; protons of the sugar |
| | 6.3 ppm | 1 H; doublet; 3-H |
| | 6.9 ppm | 1 H; singlet; 8-H |

-continued

Proton NMR in DMSO-d-TMS internal reference. Varion EM 360

| | | |
|---|---|---|
| | 7.4 ppm | 1 H; singulet; 5-H |
| | 7.9 ppm | 1 H; doublet; 4-H phenolic OH peak very broad |
| No. 18 | 1.1 ppm | 3 H; doublet; CH₃ of rhamnose |
| | 1.2 and 1.4 ppm | 2 × 3 H; singlets; exo and endo-isopropylidene CH₃'s |
| | 2.5–5.8 ppm | 22 H; complex multiplet; CH, OH and CH₂ protons of the sugars + 2,3,3-H protons and 4'-OCH₃ at 3.8 ppm |
| | 6.1–6.3 ppm | 2 H; complex multiplet; 6,8-H |
| | 6.8–7.1 ppm | 3 H; complex multiplet; 2', 5', 6'-H |
| | 9 ppm | 1 H; singlet; 3'-OH |
| | 12 ppm | 1 H; singlet; 5-OH |
| No. 22 | 1.1 ppm | 3 H; poorly resolved doublet; CH₃ of rhamnose |
| | 2.7–6.1 ppm | 20 H; complex multiplet; CH, OH, CH₂ protons of the sugars + acetal H + para-OCH₃ at 3.8 ppm. |
| | 6.2–7.9 ppm | 9 H; complex multiplet; aromatic protons |
| | 9–11 ppm | 3 H; broad peak; 3', 4', 7-OH |
| | 12.7 ppm | 1 H; singlet; 5-OH |
| No. 23 | 1.1 ppm | 3 H; poorly resolved doublet; CH₃ of rhamnose |
| | 2.7–6 ppm | 17 H; complex multiplet; CH, OH and CH₂ protons of the sugars + acetal H |
| | 6.2–7.8 ppm | 9 H; complex multiplet; aromatic protons |
| | 9–11 ppm | 4 H; broad peak; 3', 4', 7 + para-OH |
| | 12.7 ppm | 1 H; singlet; 5-OH |
| No. 24 | 3.1–5.7 ppm | 10 H; complex multiplet; protons of the sugar and acetal H |
| | 6.3 ppm | 1 H; doublet; 3-H |
| | 6.6–7 ppm | 4 H; complex multiplet; 8-H + protons of acetal phenyl |
| | 7.4 ppm | 1 H; singlet; 5-H |
| | 7.9 ppm | 1 H; doublet; 4-H |
| | 9 ppm | 3 H; wide peak; 3 phenolic OH's |
| No. 28 | 0.7–2.3 ppm | 19 H; complex multiplet; CH₃ of rhamnose and CH, CH₂ protons of decalin ring |
| | 2.7–5.8 ppm | 16 H; complex multiplet; CH, OH and CH₂ protons of the sugars |
| | 6.2 ppm | 1 H; doublet; 6-H |
| | 6.4 ppm | 1 H; doublet; 8-H |
| | 6.9 ppm | 1 H; doublet; 5'-H |
| | 7.4–7.7 ppm | 2 H; complex multiplet; 2', 6'-H |
| No. 32 | 0.9–1.6 ppm | 9 H; complex multiplet; CH₃ of rhamnose + 2 isopropylidene CH₃'s |
| | 2.7–5.7 ppm | 19 H; complex multiplet; CH, OH and CH₂ protons of the sugars + 4'-OMe at 3.9 ppm |
| | 6.5 ppm | 1 H; doublet; 6-H |
| | 6.7–6.9 ppm | 2 H; complex multiplet; 8,3-H |
| | 7.1 ppm | 1 H; doublet; 5'-H |
| | 7.3–7.8 ppm | 2 H; complex multiplet; 2', 6'-H |
| | 9.4 ppm | 1 H; singlet; 3'-OH |
| | 13 ppm | 1 H; singlet; 5-OH |
| No. 33 | 1 ppm | 3 H; doublet; CH₃ of rhamnose |
| | 1.3–2.3 ppm | 14 H; complex multiplet; CH, CH₂ protons of adamantane ring |
| | 2.7–5.7 ppm | 16 H; complex multiplet; CH, OH and CH₂ protons of the sugars |
| | 6.2 ppm | 1 H; doublet; 6-H |
| | 6.4 ppm | 1 H; doublet; 8-H |
| | 6.9 ppm | 1 H; doublet; 5'-H |
| | 7.4–7.7 ppm | 2 H; complex multiplet; 2', 6'-H |
| | 9–11 ppm | 3 H; broad peak; 3', 4', 7-OH |
| | 12.6 ppm | 1 H; singlet; 5-OH |
| No. 35 | 0.9 ppm | 3 H; doublet; CH₃ of rhamnose |
| | 1.4 ppm | 3 H; singlet acetal CH₃ |
| | 2.3 ppm | 3 H; singlet; para-CH₃ |
| | 2.5–5.8 ppm | 16 H; complex multiplet; CH, OH, and CH₂ protons of the sugars |
| | 6.2 ppm | 1 H; doublet; 6-H |
| | 6.4 ppm | 1 H; doublet; 8-H |
| | 6.9 ppm | 1 H; doublet; 5'-H |
| | 7.2 ppm | 4 H; center of AA'BB' system of acetal phenyl |
| | 7.4–7.7 ppm | 2 H; complex multiplet; 2', 6'-H |

-continued

Proton NMR in DMSO-d-TMS internal reference. Varion EM 360

| | | |
|---|---|---|
| | 12.6 ppm | 1 H; singlet, 5-OH very broad peak for 3', 4', 7-OH protons |
| No. 36 | 0.9 ppm | 3 H; doublet; CH₃ of rhamnose |
| | 1.4 ppm | 3 H; singlet; acetal CH₃ |
| | 2.5–5.8 ppm | 19 H; complex multiplet; CH, OH, and CH₂ protons of the sugars + para-OCH₃ at 3.8 ppm |
| | 6.2 ppm | 1 H; doublet; 6-H |
| | 6.4 ppm | 1 H; doublet; 8-H |
| | 6.6–7.9 ppm | 7 H; complex multiplet; 5', 2', 6'-H + acetal phenyl |
| | 12.4 ppm | 1 H; singlet; 5-OH very broad peak for 3', 4', 7-OH protons |
| No. 37 | 0.9 ppm | 3 H; doublet; CH₃ of rhamnose |
| | 1.4 ppm | 3 H; singlet; acetal CH₃ |
| | 2.5–5.7 ppm | 16 H; complex multiplet; CH, OH, and CH₂ protons of the sugars |
| | 6.2 ppm | 1 H; doublet; 6-H |
| | 6.4 ppm | 1 H; doublet; 8-H |
| | 6.9 ppm | 1 H; doublet; 5'-H |
| | 7.2–7.8 ppm | 6 H; complex multiplet; 2', 6'-H + acetal phenyl |
| | 9–11 ppm | 3 H; broad peak; 3', 4', 7-OH |
| | 12.6 ppm | 1 H; singlet; 5-OH |
| No. 42 | 0.8 ppm | 3 H; poorly resolved doublet; CH₃ of rhamnose |
| | 1.2–2.3 ppm | 14 H; complex multiplet; CH, CH₂ protons of adamantane |
| | 2.7–5.8 ppm | 6 H; complex multiplet; CH, OH protons of the sugar, with CH₁ at 5.8 ppm |
| | 6.2 ppm | 1 H; doublet; 6-H |
| | 6.4 ppm | 1 H; doublet; 8-H |
| | 6.9 ppm | 1 H; doublet; 5'-H |
| | 7.2–7.6 ppm | 2 H; complex multiplet; 2', 6'-H |
| | 9–11 ppm | 3 H; broad peak; 3', 4', 7-OH |
| | 12.6 ppm | 1 H; singlet; 5-OH |

TABLE I

| Compound No. | Starting Glycoside | carbonyl compound | M.P., °C. |
|---|---|---|---|
| 1 | rutin | acetone | 206 |
| 3 | quercitrin | acetone | 202 |
| 4 | 3-vicianosyl quercetin | acetone | 212 |
| 5 | isoquercitrin | acetone | 236 |
| 6 | rutin | cyclohexanone | 238 |
| 7 | quercitrin | cyclohexanone | 240 |
| 8 | naringin | acetone | 240 |
| 15 | esculin | acetone | 228 |
| 16 | esculin | cyclohexanone | 145 |
| 18 | hesperidin | acetone | 155 |
| 22 | rutin | MeO—⌬—C(=O)—H | 202 |
| 23 | rutin | HO—⌬—C(=O)—H | 230 |
| 28 | rutin | 2-decalone | 250 |
| 32 | diosmin | acetone | 256 |
| 33 | rutin | 2-adamantanone | 240 |
| 35 | rutin | Me—⌬—C(=O)—CH₃ | 248 |
| 36 | rutin | MeO—⌬—C(=O)—CH₃ | 249 |
| 37 | rutin | Cl—⌬—C(=O)—CH₃ | 224 |

TABLE I-continued

| Compound No. | Starting Glycoside | carbonyl compound | M.P., °C. |
|---|---|---|---|
| 42 | quercitrin | 2-adamantanone | 200 |

Solubilities in water in g/l
Rutin (0.12); No. 1 (7); No. 6 (<0.1)
Quercitrin (insoluble); No. 3 (1.6); No. 7 (<0.1)
3-Vicianosyl quercetin (0.33); No. 4 (0.6)
Isoquercitrin (insoluble); No. 5 (<0.1)
Esculin (1.7); No. 15 (9.2); No. 16 (1.25)
Hesperidin (0.02); No. 18 (0.9)

The biological and pharmacological properties of representative compounds of the present invention are described below:

Inhibition of Aldose Reductase In Vitro

The enzyme is extracted from beef eye lenses and its activity was measured using glyceraldehyde as a substrate, according to the method described by Hayman et al, J. Biol. Chem. 240 (2), 877 (1965). The reoxidation of NADPH coupled to the enzymatic reaction was followed spectrophotometrically at 340 nm.

Table II shows the percentages of inhibition due to the compounds of the present invention as well as to reference compounds in DMF solution, as a function of their concentration in the medium expresses in mole/l.

TABLE II

| Compound | Concentration | $10^{-4}$ | $5.10^{-5}$ | $10^{-5}$ | $5.10^{-6}$ | $10^{-6}$ | $5.10^{-7}$ | $10^{-7}$ |
|---|---|---|---|---|---|---|---|---|
| No. 1 | | 82 | 69 | 32 | 13 | | | |
| No. 3 | | 100 | 96 | 92 | 92 | 80 | 74 | 40 |
| No. 4 | | 42 | 17 | 0 | | | | |
| No. 5 | | 83 | 83 | 56 | 33 | 0 | | |
| No. 6 | | 93 | 86 | 66 | 50 | 10 | | |
| No. 7 | | 91 | 91 | 95 | 91 | 84 | 87 | 87 |
| No. 8 | | 25 | 19 | 0 | | | | |
| No. 14 | | 93 | 100 83 | | 33 | 11 | 0 | |
| No. 15 | | 60 | 44 | 9 | | | | |
| No. 16 | | 63 | 50 | 14 | | | | |
| No. 22 | | 92 | 89 | 79 | 43 | 0 | | |
| No. 23 | | 80 | 70 | 41 | 12 | | | |
| No. 24 | | 71 | 62 | 0 | | | | |
| No. 28 | | 67 | 67 | 62 | 44 | 0 | | |
| No. 33 | | 100 | | 92 | 82 | 44 | 33 | 7 |
| No. 35 | | 100 | | 72 | | 26 | 17 | |
| No. 36 | | 100 | | 69 | | 22 | 13 | |
| No. 37 | | 100 | | 59 | | 24 | 4 | |
| Rutin | | 48 | 27 | 6 | | | | |
| | | 86 | 58 | 0 | | | | |
| | | 72 | 57 | 24 | 0 | | | |
| | | 75 | 60 | 20 | 0 | | | |
| Ethoxazorutin | | 38 | 6 | 0 | | | | |
| Hydroxyethylrutin | | 30 | 0 | | | | | |
| Naringin | | 33 | 8 | | | | | |
| Esculin | | 16 | 0 | | | | | |
| Myricitrin | | 83 | | 56 | 50 | 9 | | |

Inhibition of COMT in vitro

The enzyme is extracted from rat liver by the method described by Axelrod et al, J. Biol. Chem., 233, 702(1958); its activity is measured in the presence of S-adenosyl methionine and using as substrate 4-nitrocatechol by the method described by Lee et al, J. Pharm. Sci., 66(7), 986(1977). The quantity of 4-nitrocatechol consumed was determined spectrophotometrically at 520 nm in alkaline medium.

Table III shows the percentages of inhibition due to the compounds of the present invention as well as to rutin in dimethylsulfoxide solution, as a function of their concentration in the medium expressed in mole/l.

TABLE III

| Compound | Concentration | $10^{-3}$ | $10^{-4}$ | $5.10^{-5}$ | $10^{-5}$ | $5.10^{-6}$ |
|---|---|---|---|---|---|---|
| 22 | | 80-100 | 80-92 | 87 | 45 | 25 |
| 23 | | 80 | 90 | 54 | 40 | 27 |
| 28 | | 76 | 52 | | 0 | |
| 33 | | 96-93 | 81-83 | 53 | 33-36 | |
| 35 | | 90 | 74 | 69 | 72 | 55 |
| 36 | | 91 | 83-79 | 58-58 | 15-22 | |
| 37 | | 100 | 74 | | 27 | |
| Rutin | | 63-68 | 57-53 | 47 | 13 | |

Anti-inflammatory activity

This was determined by the carragenin edema test using male Wistar EOPS rats. Inflammation was induced by the injection of 0.1 ml of a suspension of 5% carragenin in physiological serum into the muscular bundle of the metatarsal region of the posterior paw of the animal. The test substance was administered i.p. in neutralized solution at the same time as the carragenin.

Edema was measured by plethysmometry at different times after the administration of the carragenin.

Tables IV and V show the percentages of inhibition as a function of time and of dosage for certain compounds of the present invention.

TABLE IV

| Compound | Solution Medium | dose in mg/kg | % inhibition of carragenin edema as a function of time | | | | | | | | |
|---|---|---|---|---|---|---|---|---|---|---|---|
| | | | ½ h | 1 h | 1 h ½ | 2 h | 3 h | 4 h | 5 h | 6 h | 24 h |
| No. 1 | Physiological serum | 100 | 33 | 24 | | 5 | 7 | 16 | 20 | 7 | |
| | | 200 | 0 | 0 | | 8 | 8 | 12 | 15 | 9 | |
| | | 300 | 30 | 37 | | 8 | 16 | 27 | 30 | 27 | |
| | | 75 | 18 | 18 | 29 | 23 | 20 | 14 | 25 | 17 | 5 |

TABLE IV-continued

| Compound | Solution Medium | dose in mg/kg | % inhibition of carragenin edema as a function of time | | | | | | | | |
|---|---|---|---|---|---|---|---|---|---|---|---|
| | | | ½ h | 1 h | 1 h ½ | 2 h | 3 h | 4 h | 5 h | 6 h | 24 h |
| | Borate buffer pH 7 | 150 | 15 | 25 | 40 | 34 | 26 | 19 | 27 | 28 | 21 |
| | | 200 | 9 | 16 | 37 | 38 | 30 | 21 | 30 | 18 | 0 |
| | | 75 | 26 | 0 | 0 | 10 | 6 | 3 | 6 | 10 | 21 |
| No. 3 | Borate buffer pH 7 | 100 | 45 | 55 | 41 | 30 | 19 | 18 | 19 | 18 | 17 |
| | | 150 | 26 | 0 | 0 | 20 | 0 | 2 | 3 | 8 | 11 |
| | | 200 | 40 | 45 | 12 | 0 | 0 | 0 | 2 | 1 | 0 |
| | | 35 | 26 | 32 | 23 | 33 | 9 | 7 | 10 | 14 | 27 |
| No. 6 | Borate buffer pH 7 | 40 | 28 | 23 | 11 | 7 | 2 | 5 | 2 | 0 | 26 |
| | | 75 | 29 | 9 | 3 | 14 | 17 | 0 | 7 | 13 | 21 |
| | | 100 | 23 | 20 | 9 | 1 | 2 | 10 | 15 | 5 | 37 |
| | | 200 | 14 | 19 | 2 | 4 | 0 | 8 | 9 | 1 | 0 |
| | | 50 | 0 | 14 | 22 | 16 | 23 | 21 | 7 | 6 | 10 |
| No. 7 | Borate buffer pH 7 | 75 | 48 | 73 | 91 | 89 | 86 | 81 | 83 | 81 | 84 |
| | | 100* | 21 | 51 | 52 | 48 | 45 | 46 | 45 | 43 | 67 |
| | | 150** | 70 | 89 | 97 | 97 | 94 | 89 | 91 | 86 | 87 |
| | | 50 | 0 | 0 | 0 | 0 | 0 | 0 | 0 | 0 | |
| quercetin | Saturated bicarbonate solution | 100 | 2 | 0 | 8 | 7 | 0 | 0 | 0 | 0 | |
| | | 75 | 28 | 32 | | 18 | 28 | 22 | 23 | 25 | |
| Isoquercitrin | Saturated bicarbonate solution | 150 | 30 | 40 | | 37 | 18 | 9 | 9 | 6 | |

*20% mortality in 24 h
**80% mortality in 5 h

TABLE V

| Compound | dose in mg/kg | % inhibition of carragenin edema as a function of time | | | | | | | |
|---|---|---|---|---|---|---|---|---|---|
| | | ½ h | 1 h | 1 h ½ | 2 h | 3 h | 4 h | 5 h | 6 h |
| No. 8 | 100 | 23 | 64 | 85 | 75 | 48 | 48 | 35 | 37 |
| | 200 | 9 | 42 | 70 | 60 | 28 | 27 | 22 | 24 |
| | 300 | 62 | 78 | 74 | 73 | 50 | 50 | 33 | 35 |
| No. 18 | 100 | 0 | 0 | 17 | 16 | 13 | 20 | 21 | 27 |
| | 200 | 0 | 18 | 39 | 42 | 46 | 52 | 50 | 55 |
| | 300 | 0 | 0 | 27 | 27 | 21 | 26 | 16 | 16 |
| No. 15 | 200 | 18 | 26 | 20 | 13 | 1 | 7 | 10 | 17 |
| No. 16 | 200 | 59 | 59 | 45 | 46 | 30 | 23 | 27 | 24 |
| No. 32 | 150 | 5 | 17 | 37 | 49 | 43 | 42 | 37 | 34 |
| | 200 | 8 | 16 | 35 | 43 | 36 | 30 | 20 | 20 |
| | 300 | 0 | 8 | 38 | 44 | 31 | 32 | 43 | 36 |

The above results were obtained for solutions of substantially alkaline pH.
The reference experiments were performed using physiological serum brought to a pH approximately the same as the pH of the solutions to be tested.

Capillaroprotecting effects

The capillary resistance was determined by a variant of the method of Charlier et al, Arch. Inter. Physiol. Biochem., 71, 1–45 (1963) on male OFA EOPS rats.

The capillary permeability was determined by the method of Charlier et al, Arch. Inter. Physiol. Biochem., 71, 51–63 (1963) using conventional male Wistar rats.

The compounds were administered i.p. in neutralized solution (borate buffer for compounds No. 5 and 6).

Table VI shows the capillary resistance effect observed, in units of cm Hg/h as well as the percentage of animals showing an effect greater than or equal to 25 μcm Hg/h as a function of the dose administered.

Table VII shows the percentage of reduction of capillary permeability as a function of the dose.

GALACTOSEMIC CATARACT IN RATS

The study was conducted using weaning male EOPS Wistar rats having an initial weight of between 45 and 50 g. The animals were fed a high vitamin and high protein regimen containing 20% by weight of galactose. The first signs of cataracts, detected by the ophthalmoscope, appeared beginning with the third day. The animals received daily i.p. doses of the test compound, the treatment being started four days after the commencement of the galactosemic regimen. The evolution of the cataract was followed by the detection of maroon rings visible in the ophthalmoscope. These rings appeared on the external edge of the lens and progressed little by little to its center. Anatomopathological studies of the lenses confirmed that these brown rings correspond well to the characteristic histological lesions of galactosemic cataracts. Photographs taken with the aid of a retinograph facilitated the comparison of the evolution of the lesions.

TABLE VI

| | CAPILLARY RESISTANCE | | |
|---|---|---|---|
| Compound | dose mg/kg | effect observed u cm Hg/h | % of animals for which the effect is ≧25 u cm Hg/h |
| No. 1 | 100 | 21.5 ± 4.6 | 50 |
| | 200 | 41.25 ± 15.3 | 90 |
| No. 3 | 50 | 19.5 ± 7.4 | 40 |
| | 100 | 34.75 ± 11.1 | 80 |
| | 200 | 56 ± 11.3 | 100 |
| No. 5 | 50 | 28 ± 9.8 | 60 |
| | 100 | 32.25 ± 11.4 | 80 |
| | 200 | 37 ± 16.1 | 80 |
| No. 6 | 50 | 19.75 ± 10.2 | 30 |
| | 100 | 25.5 ± 13.2 | 40 |
| | 200 | 37.75 ± 12.9 | 90 |
| No. 15 | 25 | 17 ± 11.8 | — |
| | 50 | 20 ± 12.9 | — |
| No. 16 | 25 | 8.8 ± 6.8 | — |
| | 50 | 23 ± 11.1 | — |
| | 50 | 20.75 ± 10 | 40 |
| Ethoxazorutin | 100 | 18.75 ± 7.5 | 20 |
| | 200 | 34.75 ± 10.8 | 80 |
| Hydroxyethyl-rutosides | 100 | 17.5 ± 9.2 | 20 |
| | 200 | 21 ± 13.2 | 50 |

TABLE VII

PERCENTAGE REDUCTION OF CAPILLARY PERMEABILITY

| Compound | Dose mg/kg | | | | | | | | |
|---|---|---|---|---|---|---|---|---|---|
| | 10 | 40 | 50 | 75 | 100 | 200 | 300 | 400 | 800 |
| No. 1 | | | | | | | | 30 | 37 |
| No. 3 | | | 21 | | 25 | 59 | | | |
| No. 5 | | | 11 | | 34 | 28 | | | |
| No. 6 | | | 21 | | 20 | 23 | | | |
| No. 18 | 24 | | 21 | 8 | | | | | |
| No. 32 | 7 | | | 32 | | | | | |
| Ethox- | | | | | | | | | |

TABLE VII-continued

PERCENTAGE REDUCTION OF CAPILLARY PERMEABILITY

| Compound | Dose mg/kg | | | | | | | | |
|---|---|---|---|---|---|---|---|---|---|
| | 10 | 40 | 50 | 75 | 100 | 200 | 300 | 400 | 800 |
| azo-rutine | | 20 | | | 11 | 26 | | | |
| Hydroxyethyl-rutoside | | | 25 | | 5 | | 0 | | 24 |

Table VIII shows the evolution with time of the precentage of animals which have not yet shown the appearance of cataracts, as a function of the treatment.

Table VIII

| treatment | time in days | | | | | | | | | | |
|---|---|---|---|---|---|---|---|---|---|---|---|
| | −4 | 0 | 1 | 2 | 3 | 4 | 5 | 6 | 10 | 12 | 16 |
| Physiological serum | 100 | 100 | 100 | 84 | 62.5 | 6 | 0 | 0 | 0 | 0 | 0 |
| 3-Vicianosyl quercetin 100 mg/kg/d i.p. | 100 | 100 | 100 | 97 | 59 | 40 | 31 | 12 | 9 | 19 | 22 |
| | | | | NS | NS | S | S | S | NS | S | S |
| Compound No. 1 100 mg/kg/d i.p. | 100 | 100 | 100 | 87.5 | 81 | 50 | 37.5 | 37.5 | 37.5 | 28 | 19 |
| | | | | NS | NS | S | S | S | S | S | S |

NS = Not significant
S = Significant

Statistical calculations according to the $\chi^2$ method permit an evaluation of the significance of the results obtained for each of the treatments compared to those for non-treated animals.

Toxicity

The acute toxicity of the compounds of the present invention was determined in mice. Compound No. 3 was administered i.p. in neutralized borate buffer solution to OF1 EOPS mice, and did not result in mortality until a dose of 400 mg/kg over a duration of 7 days.

The i.p. toxicities of certain compounds of the present invention were determined using male and female Swiss EOPS mice for administrations in DMSO solution at ½ under a volume of P/100. The percentages of mortality at the end of 14 days are shown in Table IX.

TABLE IX

| Compound | Dose in mg/kg | | | | |
|---|---|---|---|---|---|
| | 500 | 750 | 1000 | 1500 | 2000 |
| No. 8 | 0 | | 0 | | 0 |
| No. 15 | 10 | | 0 | 20 | 70 |
| No. 16 | 10 | 80 | 80 | | |
| No. 18 | | | 0 | | 0 |
| No. 32 | | | 0 | | |

The minimum lethal dose of compound No. 1 administered by slow i.v. perfusion in the Wistar EOPS rat is in the neighborhood of 15 mg/kg/min. for 30 min. A brief, low intensity hypotension is observed accompanied by bradycardia. The arterial pressure and the cardiac frequency then rise and attain their maximum values at the twelfth minute of the perfusion, then diminish progressively until death occurs by respiratory arrest.

In view of their properties, the compounds of the present invention may be used in therapy wherever benzopyran glycosides are normally indicated such as for vasculopathies characterized by a fragilization of the wall or high risk vascular conditions; for example, varices, hemmorhoids, edemas, purpuras, arterial hypertension, hemorrhagic syndromes, glomerulonephritis, ischemic cardiopathies, hepatic insufficiency, and diabetes. Furthermore the inhibitory effects on aldose reductase shown by these compounds allows them to be used for the prevention and treatment of metabolic cataracts or diabetic neuropathies.

The active principle, together with appropriate excipients, may be administered as follows:

orally (preferably in a gastro-resistant form such as coated tablets, microcapsules) at doses of 50–600 mg/d in two or three daily administrations;

rectally (suppositories, rectal capsules) at doses of from 50 mg to 1 g/d in one or two daily administrations;

parenterally (subcutaneous, intramuscular or intravenous injections) at doses of from 0 to 500 mg/d in one or two daily injections;

topically in a form of ointments, jellies or creams.

For the special treatment of diabetic retinopathies or metabolic cataracts, an ophthalmological jelly or eye wash may be used.

The active principle may be used in association with other active substances such as vasodilators, spasmolytics, local anesthetics, ascorbic acid or anti-inflammatories.

The following non-limiting examples illustrate various formulations.

| Injectable solutions | | |
|---|---|---|
| Active principles | Compound No. 15 | 0.030 g |
| | nicotinic acid | 0.050 g |
| Excipient | qsp | 2 ml ampoule |
| Active principle | Compound No. 1 | 0.025 g |
| | nicotinic acid | 0.050 g |
| Excipient | qsp | 2 ml ampoule |
| Gastro Resistant Tablets | | |
| Active principles | Compound No. 33 | 0.10 g |
| | mesoinositol | 0.25 g |
| Excipient | qsp gastro-resistant tablet | |
| Active principles | Compound No. 32 | 0.30 g |
| | ascorbic acid | 0.20 g |
| Excipient | qsp gastro-resistant tablet | |
| Active principles | Compound No. 7 | 0.15 g |
| | ascorbic acid | 0.20 g |
| Excipient | qsp gastro-resistant tablet | |
| Suppositories | | |
| Active principles | Compound No. 42 | 0.10 g |
| | amylain chlorhydrate | 0.03 g |
| Excipient | qsp | one suppository |
| Active principles | Compound No. 1 | 0.200 g |
| | butoform | 0.025 g |
| Excipient | qsp | one suppository |

| Eye Wash | | |
|---|---|---|
| Active principles | Compound No. 7 | 1.00 g |
| Excipient | Boric acid sodium borate, methyl para-hydroxybenzoate distilled water | |
| | qsp | 100 ml |
| Ointments | | |
| Active principles | Compound No. 5 | 1.00 g |
| | dextran sulfate | 0.30 g |
| Excipient | qsp | 100 g |
| Active principles | Compound No. 8 | 1.00 g |
| | lignocaine chlorhydrate | 2.00 g |
| Excipient | qsp | 30 g |

Having fully described this invention, it will be apparent to one of ordinary skill in the art that many changes and modifications can be made thereto without departing from the spirit or scope of the invention set forth therein.

What is claimed as new and intended to be covered by Letters Patent is:

1. A benzopyran glycoside acetal or ketal at the sugar portion of the glycoside of a benzopyran glycoside selected from the group consisting of myricitrin, esculin, hesperidin, narigin, diosmin and glycosides of quercitin, and a carbonyl compound selected from the group consisting of wherein $R_1$ and $R_2$ are the same or different and $R_1$, $R_2$=H, lower alkyl, phenyl, phenyl substituted by one or more substituents selected from the group consisting of hydroxyl, lower alkoxyl, halogen, nitro, amino, lower alkyl, and carboxyl, but excluding $R_1=R_2=H$;

wherein n=4–7; 2-adamantanone, 1-decalone, 2-decalone, said benzopyran glycoside acetal or ketal and said benzopyran glycoside containing phenolic hydroxyl.

2. The benzopyran glycoside acetal or ketal of claim 1, wherein said benzopyran glycoside is rutin, quercetin, 3-vicianosyl quercitin or isoquercitrin.

3. The benzopyran glycoside acetal or ketal of claim 1, wherein said carbonyl compound is acetone.

4. The benzopyran glycoside acetal or ketal of claim 1, wherein said carbonyl compound is selected from the group consisting of acetone, 2-adamantanone and cyclohexanone, and said benzopyran glycoside is one of rutin or quercitrin.

5. The benzopyran glycoside acetal or ketal of claim 1, wherein said benzopyran glycoside is one of rutin or quercitrin and said carbonyl compound has the formula wherein E=H or one or more substituents selected from the group consisting of hydroxyl, alkoxyl, halogen, nitro, amino, lower alkyl, and carboxyl.

6. A method of preparing the benzopyran glycoside acetal or ketal of claim 1 which comprises the steps of dissolving a benzopyran glycoside in a polar solvent, adding a solution of a carbonyl compound as defined in claim 1, paraldehyde or a dimethyl or diethyl acetal of the carbonyl compound, and then adding with agitation a condensing agent selected from the group consisting of ethyl, methyl or benzyl chloroformate.

7. The method of claim 6, wherein said polar solvent is dimethyl formamide and said carbonyl compound is acetone.

8. A medicament comprising an acetal or ketal of claim 1 as its active principle, in combination with a pharmaceutically acceptable vehicle.

9. The benzopyran glycoside ketal of claim 2 which is 3-O(2,3-O,O-isopropylidene-6-α-L-rhamnosyl-β-D-glucosyl)-quercetin.

* * * * *